United States Patent [19]

Schwarz

[11] Patent Number: 5,401,977
[45] Date of Patent: Mar. 28, 1995

[54] METHOD AND APPARATUS FOR GLOSS MEASUREMENT WITH REFERENCE VALUE PAIRS

[75] Inventor: Peter Schwarz, Geretsried, Germany

[73] Assignee: BYK-Gardner GmbH, Geretsried, Germany

[21] Appl. No.: 674,365

[22] PCT Filed: Oct. 13, 1989

[86] PCT No.: PCT/EP89/01218

§ 371 Date: Jun. 11, 1991

§ 102(e) Date: Jun. 11, 1991

[87] PCT Pub. No.: WO90/04166

PCT Pub. Date: Apr. 19, 1990

[30] Foreign Application Priority Data

Oct. 14, 1988 [DE] Germany ............ 38 35 065.3

[51] Int. Cl.6 .................. G01N 21/86; G01N 21/55
[52] U.S. Cl. .................................... 250/559; 356/448
[58] Field of Search ........ 250/572, 571, 559, 562–563, 250/223 R; 356/445, 448, 446

[56] References Cited

U.S. PATENT DOCUMENTS

| | | | |
|---|---|---|---|
| 3,999,864 | 12/1976 | Mutler | 356/416 |
| 4,455,090 | 6/1984 | Roberts | 356/448 |
| 4,566,798 | 1/1986 | Haas | 356/448 |
| 4,583,861 | 4/1986 | Yamaji et al. | 356/448 |
| 4,750,140 | 6/1988 | Asano et al. | 356/445 |
| 4,766,551 | 8/1988 | Begley | 356/448 |

FOREIGN PATENT DOCUMENTS 2014295 10/1970 Germany .
2448288 1/1976 Germany .
3413838 10/1984 Germany .

Primary Examiner—David C. Nelms
Assistant Examiner—Michael Messinger
Attorney, Agent, or Firm—Leydig, Voit & Mayer

[57] ABSTRACT

An apparatus and method for measuring the gloss of a surface with a light source projecting light in the direction of the surface and a light-sensitive sensor receiving the light reflected from the surface and converting it into an electrical signal value. A memory storing a program for calculating the characteristic gloss value, a computer for calculating a characteristic gloss value from the electrical signal value, and a display for visually displaying the calculated characteristic gloss value are provided. Five or more reference value pairs are stored in the memory, each pair consisting of a reference characteristic gloss value and a corresponding reference electrical signal value measured by the apparatus on the basis of the reference surface. The measured electrical signal value is compared with the reference signal values and at least the next higher and the next lower value for interpolating the measured gloss.

11 Claims, 3 Drawing Sheets

METHOD AND APPARATUS FOR GLOSS MEASUREMENT WITH REFERENCE VALUE PAIRS

FIELD OF THE INVENTION

The present invention relates to a apparatus and a method for the measurement of gloss.

BACKGROUND OF THE INVENTION

Gloss is an important quality criterion e.g. for assessing the quality of paints, coatings, plastic surfaces and the like. Measuring gloss with results that are repeatable and decisive is, however, exceptionally difficult. From a physical point of view gloss can be defined as the property of a surface in its ability to reflect light. But the human eye fails to "see" this physical aspect, instead there are considerable physiological deviations which make it difficult to standardize the results of gloss measurements.

In Germany there is a draft proposal for an industrial standard—DIN 67 350—which dates back to November 1980 and in which a reflectance method for measuring gloss is proposed as a standard. In this method light from a light source is projected on the surface to be measured and introduced from this surface via a lens into a photocell. Since even slight deviations in the position of the optical components result in a considerable change of the light incident on the photocell, the angle of aperture of the diaphragms used and the alignment of the individual optical components must be exceptionally precise.

Known devices working according to this method feature an aluminum carrier for the optical components. These devices are calibrated by measuring a standard surface having a very high characteristic gloss value, i.e. a high-gloss surface and so-called light trap. A light trap is a surface having no reflectance whatsoever and thus has a gloss value of zero. In the known measurement device it is assumed that the characteristic gloss value, contrary to the physiological considerations, has a linear profile between the value 0 and a high-gloss value. To minimize deviations due to lack of exactness in the geometry of the optical components, there; is the possibility in these known devices of, for instance, distorting the aluminum carrier of the optical components to precisely align the optical components.

A similar method of measuring surface gloss is proposed as a standard also from the International Standard ISO 2813/1978 dating back to the year 1978. In the USA the measurement of gloss is standardized by the ASTM D 523 standard.

DE-OS 34 13 838 discloses an instrument for measuring gloss in which a plurality of sets of optical means is arranged within the instrument so that the reflectance can be measured at differing angles of incidence. For this purpose measuring detectors are provided which receive the reflected light and the electrical output signals of which are evaluated by calculating means. To enable this to be done, a reference value is held in the memory of the device for each set of optical means, this reference value corresponding to the signal as measured at a characteristic gloss value of 100. The intermediate values are then obtained by division.

Practical experience with known devices for measuring gloss indicate that it would be highly desirable to improve the accuracy of these instruments. In addition, it is also known that it is very difficult to achieve the necessary accuracy when adjusting by means of distorting the carrier.

SUMMARY OF THE INVENTION

The present invention thus has the object of creating a apparatus and method for measuring gloss which furnish considerably more accurate results than formerly possible with instruments of prior art.

The apparatus according to the invention has the advantage that computing the characteristic gloss value can be achieved with much higher accuracy than hitherto possible.

The method according to the invention constitutes a completely new method of evaluating gloss measurements. Until now, gloss measurements were evaluated highly insufficiently by linearly relating the reference reflectance measurement to the characteristic gloss value. The method according to the invention thus provides for holding (saving) a minimum of 5, but preferably 10 or more pairs of reference values in the apparatus for each set of optical means. These pairs of reference values are obtained by measuring the reflectance of reference surfaces which in Germany, for instance, can be obtained from the Berlin Institute of Material Testing and the corresponding characteristic electrical signals then be saved in the device. Each pair in this respect then comprises the actual reference characteristic gloss value and the electrical signal value as measured within the apparatus. When, for example, 10 reference characteristic gloss values are measured in the range from 0 to 93, the corresponding electrical signal values are then stored with these values.

In a measurement the obtained electrical signal value is compared to the stored signal values, it then being established between which values the measured signal value lies. Subsequently the associated characteristic gloss values are interpolated.

By means of this method according to the invention it is thus possible to approximate the non-linear profile of the curve representing the characteristic gloss values of the reflectance in a substantially more accurate way than made possible by prior art using a simple linear approximation.

One substantial advantage of the apparatus according to the invention is that characteristic gloss values can be measured which lie above that of high gloss (characteristic gloss value 93). For the special case of ideal reflectance a value of 1000 is used as the basis for the characteristic gloss. For a more or less ideal mirror surface this value is approx. 980. It is now possible to save this value of 980 as the highest value for the characteristic gloss as the corresponding electrical signal value for this high-gloss mirror surface. When 10 reference values are used, this would be the tenth value; when 16 reference values are used it would be the sixteenth value. The apparatus can then reliably detect characteristic gloss values between 0 and 980 and is then also suitable for measuring mirror gloss which is not possible with devices of the prior art.

The device according to the invention is configured to carry out this reference measurement individually for each apparatus. The pairs of values held in the memory thus correspond to the measured values as obtained by each individual apparatus, thus making deviations from one apparatus to another due to fabrication variations irrelevant.

In a technical context the terms "calibrate" and "final adjustment" are often used in the same sense. To distinguish the two, "calibration" in the following means reading the pairs of reference values into the device, i.e. "calibrate" in this sense means setting the basic relationship between the measured parameter and the indicated value of the characteristic gloss, whereas "final adjustment" ("recalibration") denotes correction of the reference values held in the memory.

In accordance with one of the preferred embodiments of the apparatus according to the invention, the device includes a microprocessor, preferably provided as a single-chip computer, for implementing the comparison operations and the necessary interpolation operations.

In accordance with a further preferred embodiment the apparatus is configured so that establishing the pairs of reference values is controlled by a processor outside of the instrument. This has the advantage that no program needs to be held in the memory of the instrument to carry out calibration of the instrument. In this case, the instrument features a suitable multi-pin receptacle by means of which the integral processor (computer) can be connected to an external host computer.

The apparatus according to the invention can be fitted out with a single set of optical means comprising light source, filter, diaphragm, first lens, second lens, diaphragm and photocell. The filter is used to filter out non-visible light of the light source so that only the length waves visible to the eye are used for the measurement. Furthermore, this filter is configured to adapt the light wave spectrum to the physiological properties of the human eye. The corresponding requirements are described, e.g. in DIN 67530, with reference to other DIN standards.

In accordance with the requirements given by the measurement standard in each case, these optical means are arranged so that a desired angle of incidence to to the surface, e.g. 20°, 60° or 85° is achieved In accordance with one preferred embodiment of the invention the device is configured to feature two or three sets of optical means arranged in such a way that they exhibit the angle settings as indicated by the various standards. For instance, optical means can be arranged in the device at angles of 20°, 60° and 85° so that the requirements of the ISO Standard 2813/1978, the US standard ASTM D 523, the German standard DIN 67530 and the Japanese standard JIS 8741 can be satisfied. It is further possible to arrange the three sets of optical means at angles of 20°, 45° and 60° so that the requirements of the US Standard ASTM D 2457 can be achieved.

When only two sets of optical means are used, a selection can be made among the three values in each case. To satisfy the Japanese standard JIS Z 8741 it is sufficient to provide an arrangement of two sets of optical means, the light beam of which is angled to the surface at 20° and 60°.

Providing for three sets of optical means in such a apparatus creates, of course, more serious space accommodation problems if the device is to be maintained small and handy. To deflect the light beam, therefore, in this embodiment light guides and/or prisms of optical fiber design are used in at least one of the sets of the optical means.

In accordance with one preferred embodiment the three sets of optical means are arranged on a common mounting fixture and substantially located in a single plane. Assuming achievement of the angles of measurement 20°, 60° and 85° it is possible by means of a suitable construction to arrange the 20° and 60° measuring means so that they have a common point of incidence on the surface without the one influencing the other detrimentally. Difficulties arise, however, when integrating the 85° measuring means in such an arrangement, if this is to have essentially the same point of incidence as the 60° and 20° means. This is why the light beam is directed at a relatively steep angle, i.e. almost 90° to the surface and is deflected by a prism above the plane of the surface so that the light beam attains the desired 85° angle of deflection. By means of this embodiment it is possible to create a measuring device which satisfies all of the requirements on the standard angle of measurement in a simple way.

As explained above instruments incorporating a plurality of sets of optical means arranged at differing angles are already known from the prior art. One serious disadvantage of these instruments is, however, that they can always only measure in accordance with a single standard. When measurements need to be carried out according to various standards e.g. US, Japanese and German, then three different instruments have to be employed.

This disadvantage is eliminated by one of the preferred embodiments of the present invention by storing pairs of reference values for the various standards in the storage (memory) means. In this embodiment a selector switch is then provided so that the user can select the standard according to which he wants to measure. The instrument can then be designed to satisfy requirements to measure in two standards, i.e. in a US standard and in a German standard; however, it is also possible to design the instrument so that it permits measurements according to three or more standards, thus making merely a single instrument necessary to obtain the measured values in the different standards.

To ensure continuing accuracy of the instrument even after long-term operation means are provided in one preferred embodiment of the device for final adjustment or readjustment of the instrument. For this purpose use is made preferably of the two-parameter adjustment on the basis of a reference glass surface which is preferably high-gloss and black and exhibits a known gloss characteristic value. The instrument is then placed on this reference surface and adjusted so that it precisely achieves this reference value for the characteristic gloss .whilst retaining the measuring method of pairs of reference values as already described. The second parameter employed is the characteristic gloss value zero which being defined as producing no reflectance is simply simulated in the apparatus by switching the light source off. This final adjustment is automatically implemented by making use of a microprocessor in the instrument which prompts final adjustment automatically according to a specified program selected by a corresponding switch.

In accordance with a further preferred embodiment of the device to particularly simplify handling of final adjustment, a reference surface is already a permanent feature of the apparatus and accommodated in a suitable housing. The apparatus can then be finally adjusted easily by actuation of a switch in said housing to start the procedure of final adjustment.

As a result the invention creates a method and device for gloss measurement with substantially higher accuracy than permitted by instruments of the prior art.

BRIEF DESCRIPTION OF THE DRAWINGS

Further features of the invention result from the claims and the following description of one example of an embodiment on the basis of the drawing in which schematically

DETAILED DESCRIPTION OF THE PREFERRED EMBODIMENT

One embodiment of the apparatus according to the invention is described, as an example, in the following with reference to the FIGS. 1 thru 5.

Figure 1:
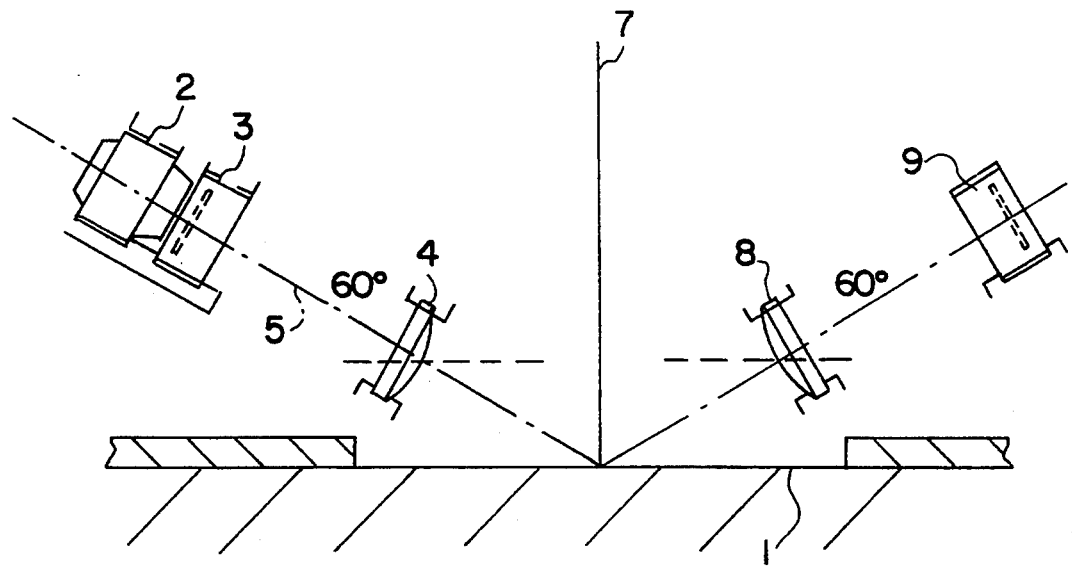
FIG. 1 shows the basic arrangement of the optical means in the apparatus according to the invention.

FIG. 1 shows the basic arrangement of the optical means for measuring gloss. On the surface being measured (1) the light beam of a light source 2 is directed. This light source 2 is an electric lamp. The light source 2 is followed by a diaphragm 3. At a certain distance away from the diaphragm 3 a first lens 4 is provided. The optical means are arranged in such a way with respect to the surface 1 that the angle of incidence of the light beam, schematically identified by 5, is 60°. This 60° angle is determined with reference to the vertical 7 on the surface 1. The reflected light is then caused to pass through a second lens 8 to enter a photocell 9.

Figure 2:
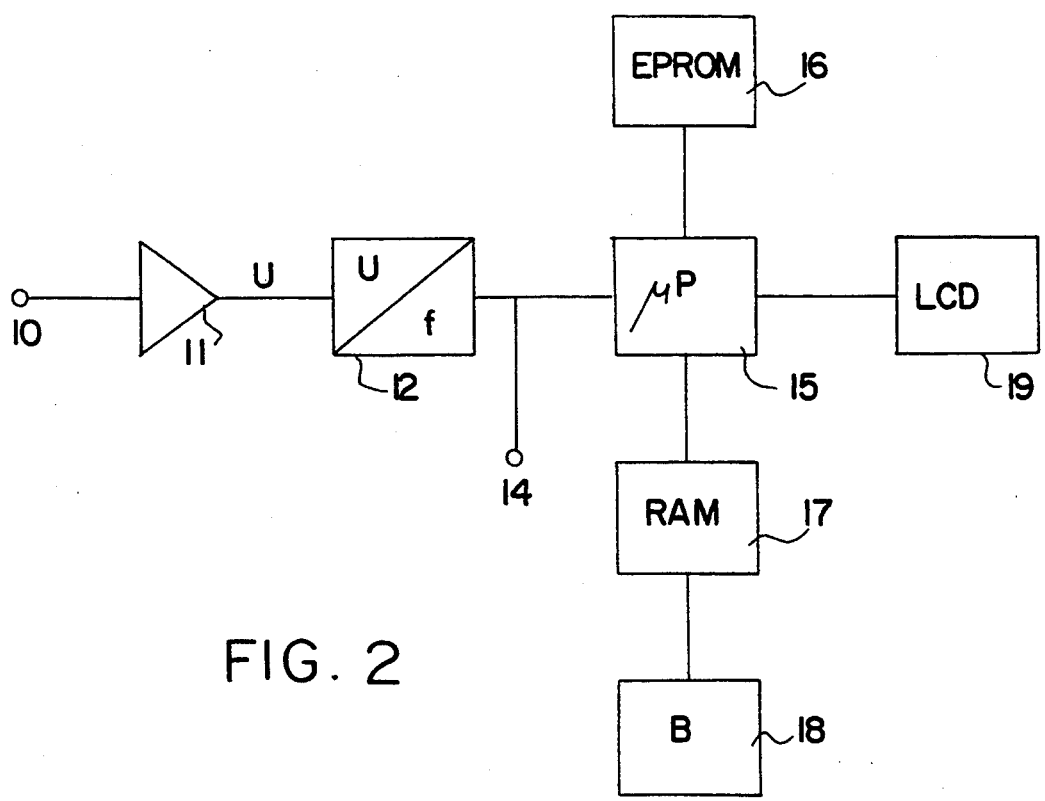
FIG. 2 shows a block diagram of how the measured value is handled.

FIG. 2 is a schematic representation of how the measured value is handled, i.e. processed. The measurement signal received by the photocell 9 is applied to the means for processing the measured value at point 10. The measurement (input) signal is first amplified in the amplifier 11. The resulting voltage is then applied to the voltage/frequency converter 12, the output signal of which is then introduced into the microprocessor 15. This microprocessor 15 is able, on the one hand, to access an EPROM 16 storing the corresponding program routines and, on the other hand, holds the pairs of reference values in memory means 17, the latter being a RAM. To reliably save the data in the memory 17 the memory means are powered via a lithium backup battery 18. The microprocessor also controls an LCD display 19 having an alphanumerical display.

Figure 3:
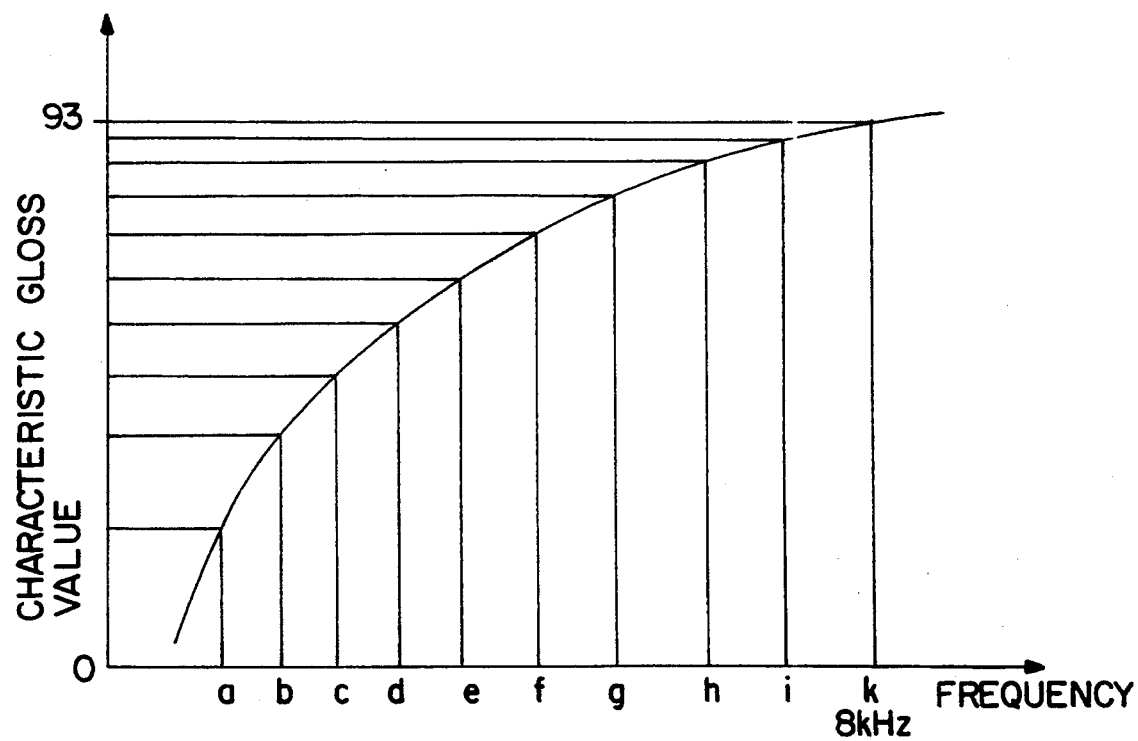
FIG. 3 shows a diagram illustrating the relationship between the measured signal and the characteristic gloss value.
Figure 4:
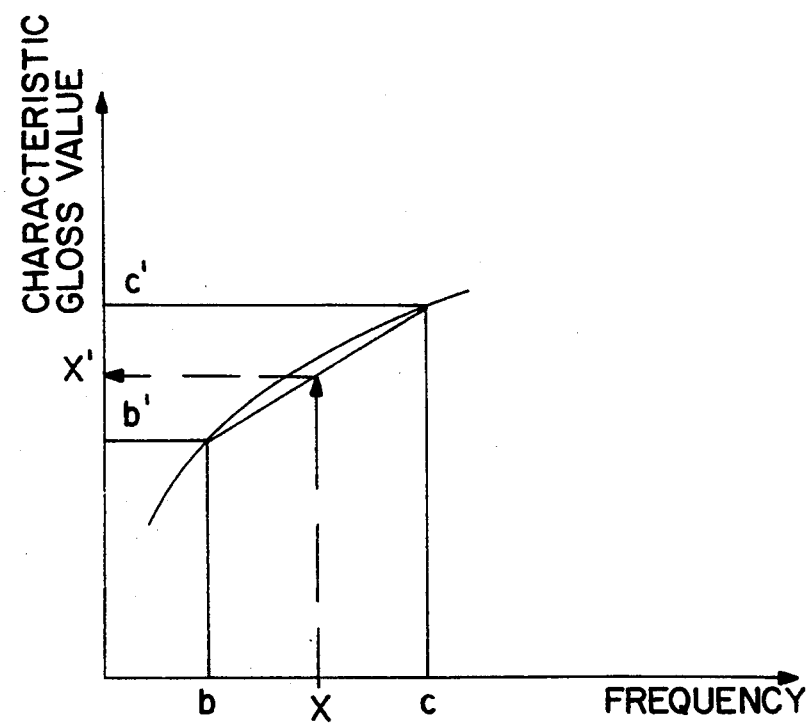
FIG. 4 is a detail of FIG. 3 to explain how evaluation is done.

Evaluation of the measurement will now be described with reference to the FIGS. 3 and 4. FIG. 3 shows a diagram, the points of which mark the frequency obtained as the result of the voltage/frequency conversion in the converter 12 of the measuring means. The ordinate indicates the characteristic gloss value pertaining to the corresponding frequency. These points are obtained by measuring reference gloss surfaces as made available by the German Institute for Material testing with the individual instrument. As can be seen from FIG. 3 the profile of the gloss/frequency relationship is non-linear. A linear approximation as done in the prior art thus results in considerable deviations of the measurement as compared to the reference values.

When a surface is to be measured the apparatus is first placed on this surface. An opening is provided at the bottom of the instrument which is dimensioned so that the light beam emitted by the light source 2 is able to impinge without restriction on the surface being measured and from which it is reflected.

The light passes through the diaphragm 3 and through the lens 4 to impinge on the surface. The reflected light is concentrated by the lens 8 and introduced into the photocell 9. The photocell 9 can operate either in the short-circuit mode, in which it furnishes a current, or in the open-circuit mode in which it furnishes a voltage. The corresponding signal of the photocell is then amplified in the amplifier 11 before being applied to the voltage/frequency converter. The resulting frequency is then compared with the individual frequency values by the microprocessor which is controlled by a program stored in the EPROM 16, these individual frequencies being each held separately in the memory means 17 of the instrument. The individual frequency values are identified by the letters a thru k in FIG. 3. The measured frequency x is thus compared to each of the frequencies to conclude e.g. that the measured frequency lies between the frequency values b and c. The characteristic gloss values belonging to these frequency values are read out of the memory 17 and by means of interpolation a characteristic gloss value x' is determined which has a corresponding relationship pertaining to the characteristic gloss values b' and c' between the frequencies b and c.

The result of the measurement is then indicated in the display 19. This display 19 is an LCD display which in the example chosen for the embodiment is an alphanumerical display, thus making it possible to provide the user with precise information as to the operating status of the apparatus at any time by means of the program routines held in the EPROM.

It should be noted that the connections as shown in FIG. 2 between the individual elements are represented merely schematically. These elements, of course, are in reality interconnected by a plurality of data lines.

Calibration of the apparatus is done as follows. 14 designates a data connection which in this example is provided as a connector on the outside of the instrument. This data connection is used to connect the measurement device to an external computer which, in conjunction with the microprocessor 15, controls the calibration procedure. For calibration the instrument is placed on one standard gloss tile after another, each featuring a different characteristic gloss value. In the host computer each characteristic gloss value of the reference surface concerned is entered. The instrument then measures the reflectance of this standard gloss title by means of the optical and electrical components incorporated in the instrument. The measured signal value together with the corresponding characteristic gloss as a reference value is then read into the memory means 17 via the host computer. This procedure is repeated for a plurality of reference surfaces. A quantity of 10–16 values has proven to be satisfactory. As soon as all pairs of reference values have been entered into the memory means 17, calibration is concluded. Since the memory means 17 in the example of the embodiment described is a volatile storage device it receives a battery backup by means of battery 18 so that the measured values are saved over a period of many years. It should be noted that it is also possible to use a non-volatile storage device such as an EEPROM.

FIG. 3 shows the profile of the curve up to the characteristic gloss value 93. As already mentioned, it is however also possible to measure higher characteristic gloss values using the measuring device according to the invention; it being possible to store the characteristic gloss values up to a value of approx. 980 together with the corresponding signal values.

As already stated there are e.g. in Germany, USA and in Japan, different standards for measuring gloss, this being the reason why until now, for instance, a paint manufacturer who wishes to state the gloss of his paints according to these differing standards had to use several gloss measuring instruments each produced and calibrated according to a specific standard. To permit measurement of gloss according to differing standards by means of a single instrument only, an embodiment of the measuring device according to the invention features a selector switch 13 shown schematically in FIG. 2 with which the instrument can be switched to the various standards, in the present case, three such standards, i.e. the user selects prior to the measurement whether he wishes to make the measurement according to the US standard, the Japanese or German standard. In the RAM 17—in this case—not only the pairs of reference values for a standard, but those of all three standards are held. Depending on the position of the selector switch 13 the microprocessor selects the corresponding pairs of values from the RAM 17.

Figure 5:
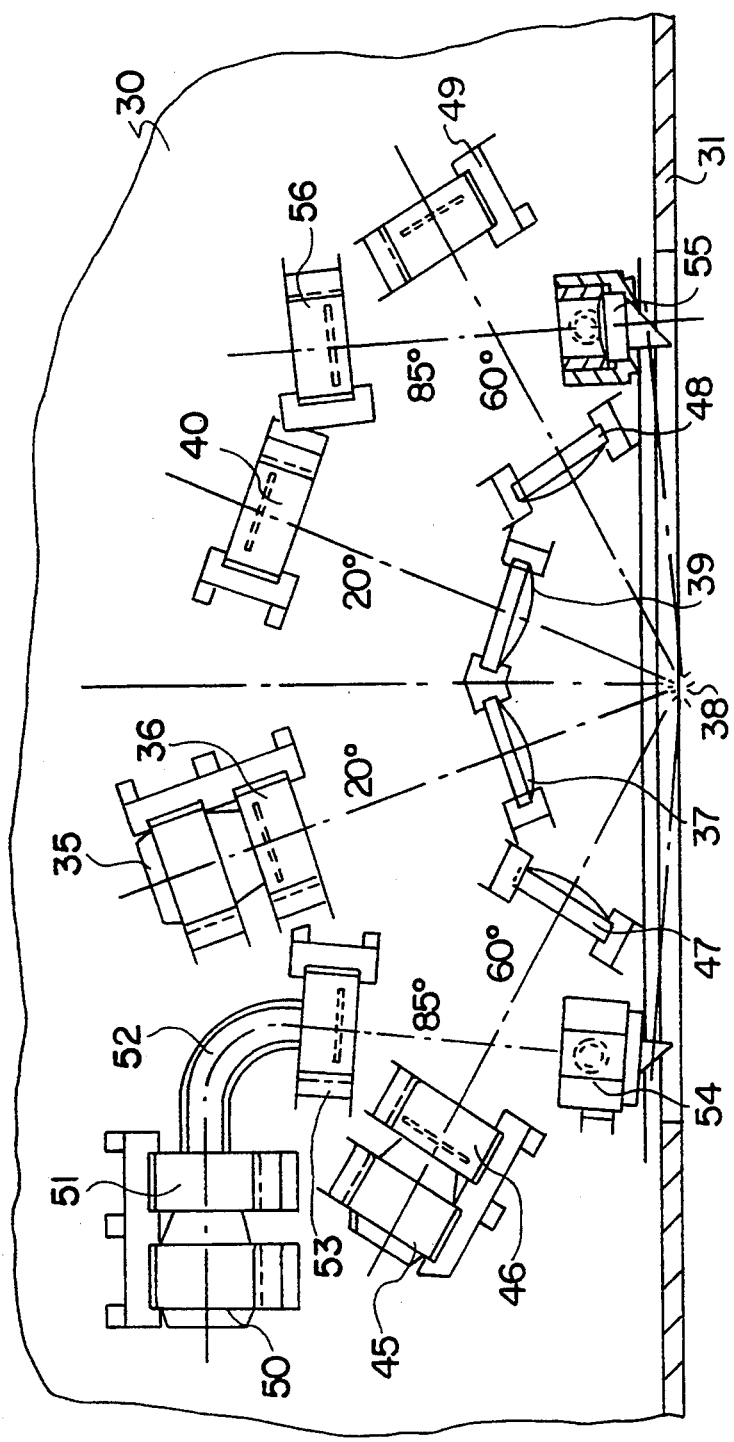
FIG. 5 shows one embodiment of the invention incorporating three sets of the optical means.

FIG. 5 shows an example of an embodiment in which three sets of optical means are used, mounted on a plastic carrier 30 and held in place by locking elements. As the first set of such means to be described, the following describers the means for projecting the light at an angle of 20° to the surface. The measurement apparatus features a plate 31 with which the device is placed on the surface to be measured. The plate 31 is arranged preferably adjustable with respect to the plastic carrier 30.

The first set of optical meanscomprises a light source 35, an electric lamp. Located directly alongside this light source 35 a component assembly 36 is provided which combines a diaphragm having a definite aperture with a filter. This filter is configured to allow only light visible to the human eye to pass. In addition this filter is designed to adapt the light to the spectral brightness sensitivity of the eye adapted to brightness. Details of this adaptation are described in German Industrial Standard DIN 5031, Part 2, DIN 5033, Part 7 and DIN 5036, Part 1.

The light beam emerging from the diaphragm passes through the lens 37 to impinge at the point 38 on the surface being measured. This point 38 is the actual point of measurement. The reflectance of the surface at point 38 is communicated back to diaphragm 40 through lens 39. The diaphragm 40 is connected to a photocell forming an assembly with the diaphragm in the example of the embodiment as shown. The electrical signal of this photocell is then applied to the signal processor as described.

A second set of optical means generates a light beam which is incident on the surface being measured at an angle of 60° at the point of measurement 38. For this purpose a light source 45 is provided as well as a diaphragm and filter 46 of the same configuration as the light source 35 and assembly 36 of the first set of optical means described. In the same way, this is then followed by the lens 47 located ahead of the point of measurement 38. The reflected light passes through the lens 48 and is incident in the assembly 49 combining the components diaphragm and photocell.

A third set of optical means is provided to produce a light beam which is incident to the surface being measured at an angle of 85° For this purpose a light source 50 is combined with a filter and a diaphragm 51. The light source and this diaphragm are arranged essentially parallel to the surface being measured. The direction of the light beam is then directed, i.e. deflected by a bundle of glass fibers 52 and caused to pass through a further diaphragm 53. From the diaphragm 53 the light then passes into a prism 54, from which it is deflected at the desired angle to the point of measurement 38. Following the point of measurement 38 a second prism 55 is provided which further deflects the light beam in the direction of an optical member 56 which is again a combination of a diaphragm and a photocell.

It should be noted that all three sets of optical means are arranged in the same plane.

To compensate for changes due to changing temperature the example of the embodiment described features a temperature-dependent resistor which is integrated in the power supply means of the light sources.

In the memory means 16 of the measuring system of the device a program routine is programmed to permit final adjustment of the apparatus. This final adjustment should not be confused with the calibration, i.e. entering the pairs of reference values since it merely serves to compensate differences caused e.g. by zero drift of the electronic components. For final adjustment the apparatus is placed on a reference surface having a high gloss value. Then the light source is first switched off so that no light can enter the photocell. After this the characteristic gloss value of zero is simulated and the zero of the measuring means adjusted accordingly. Subsequently the characteristic gloss value of the high-gloss surface is measured to provide a correcting value which is read into the RAM 17 and used in later evaluation of results.

In the examples of the embodiments of the device as described before a special protective housing is provided which surrounds the bottom part of the measuring apparatus and protects the aperture from soilage by dirt. In this protective housing a reference surface having a high gloss value is permanently incorporated. Also provided is a switch on the instrument with which final adjustment can be implemented, i.e. the instrument merely needs inserting in this protective housing and is finally adjusted automatically as soon as this switch is actuated.

The basic arrangement Figure, FIG. 2 represents this final adjustment switch by reference numeral 20.

What is claimed is:

1. An apparatus for measuring the gloss of a surface comprising:
at least one light source projecting light in the direction of a surface having a characteristic gloss being measured;
at least one light-sensitive sensor receiving light reflected from the surface and converting the reflected light into a measured electrical signal value;
storage means storing a computer program for computing the characteristic gloss of the surface from the reflected light and storing at least five reference value pairs, each reference value pair consisting of a reference characteristic gloss value and a corresponding reference electrical signal value respectively produced by the apparatus from a reference surface having a known characteristic gloss;
comparison means for comparing a measured electrical signal value with the reference electrical signal values and forwarding to the calculating means at least two reference characteristic gloss values having corresponding reference electrical signal values respectively greater and less than the measured electrical signal value;

calculating means for calculating a characteristic gloss value for the surface from the measured electrical signal value and the reference electrical signal values respectively greater and less than the measured electrical signal value by execution of the computer program; and display means for displaying the calculated characteristic gloss value.

2. The apparatus according to claim 1 wherein the light-sensitive sensor is a photocell and including, disposed between the light source and the surface, a diaphragm, a filter, and a first lens, and, disposed between the surface and the light-sensitive sensor, a second lens and a second diaphragm.

3. The apparatus according to claim 2 including at least two light sources and respective light-sensitive sensors arranged at various angles relative to the surface.

4. The apparatus according to claim 1 including a microprocessor incorporating the comparison and calculating means.

5. The apparatus according to claim 1 including interpolating means for interpolating from the two reference characteristic gloss values having corresponding reference electrical signal values respectively greater than and less than the measured signal value the characteristic gloss of the surface.

6. The apparatus according to claim 5 including a microprocessor incorporating the comparison, calculating, and interpolating means.

7. The apparatus according to claim 1 including a housing having an opening in which a surface having a known characteristic gloss may be disposed.

8. The apparatus according to claim 1 including switching means for controlling the calculating means to calculate a characteristic gloss based on a measuring standard selected by the switching means from a plurality of gloss measuring standards.

9. A method for measuring gloss comprising:

projecting light in the direction of a surface having a characteristic gloss being measured;

receiving the light reflected from the surface and converting the reflected light into a measured electrical signal value;

comparing the measured electrical signal value with at least five reference value pairs, each reference value pair consisting of a reference electrical signal value and a corresponding reference characteristic gloss value respectively produced in the apparatus from a reference surface having a known characteristic gloss;

establishing the closest lower electrical reference signal value and the closest higher reference electrical signal value relative to the measured electrical signal value; and interpolating the characteristic gloss value of the surface being measured from the reference characteristic gloss values corresponding to the closest lower and higher reference electrical signal values and the measured electrical signal value.

10. The method according to claim 9 including linearly interpolating between the closest lower and higher reference electrical signal values and comparing reference characteristic gloss values to determine the characteristic gloss value of the surface.

11. The method according to claim 9 including storing a gloss correction value based upon matching of the reference characteristic gloss values to the glosses of reference surfaces and recalibrating the reference value pairs with the gloss correction value.

* * * * *